(12) United States Patent
Allan et al.

(10) Patent No.: US 6,186,974 B1
(45) Date of Patent: Feb. 13, 2001

(54) DEVICE FOR USE IN THE EYE

(75) Inventors: Bruce Duncan Samuel Allan, London; Andrew Victor Graham Muir; Stephen Alister Jones, both of Surrey, all of (GB)

(73) Assignee: University College London and Moorfields Eye Hospital NHS Trust, London (GB)

( * ) Notice: Under 35 U.S.C. 154(b), the term of this patent shall be extended for 0 days.

(21) Appl. No.: 09/341,442

(22) PCT Filed: Jan. 12, 1998

(86) PCT No.: PCT/GB98/00085

§ 371 Date: Aug. 16, 1999

§ 102(e) Date: Aug. 16, 1999

(87) PCT Pub. No.: WO98/30181

PCT Pub. Date: Jul. 16, 1998

(30) Foreign Application Priority Data

Jan. 10, 1997 (GB) .................................... 9700390

(51) Int. Cl.[7] ................................ A61F 9/00; A61M 1/00
(52) U.S. Cl. ................................................ 604/30

(58) Field of Search ................................ 604/8, 9, 264, 604/265, 294, 30, 31; 606/166, 108, 184, 185

(56) References Cited

U.S. PATENT DOCUMENTS 5,968,058 * 10/1999 Richter et al. ...................... 606/166

\* cited by examiner

*Primary Examiner*—George Manuel
(74) *Attorney, Agent, or Firm*—Sughrue, Mion, Zinn, Macpeak & Seas, PLLC

(57) ABSTRACT

A glaucoma filtration implant is constituted by a generally tubular body section having an oblong external diameter formed of a continuous convex curve. The device preferably has flow resistance structure provided by a portion of the internal lumen having a reduced diameter. The flow resistance structure may have a length of up to 5000 $\mu$m and a diameter in the range 15 to 50 $\mu$m, the diameter being selected so as to achieve a pressure drop along the flow resistance structure in the range 5 to 15 mm Hg. The internal conduit for liquid flow also may include a removable flow inhibitor, which can be removed after implantation by a laser, such as an ophthalmic YAG laser. The device is made of biocompatible materials.

35 Claims, 7 Drawing Sheets

DEVICE FOR USE IN THE EYE

The present invention relates to a device for insertion in the eye, specifically to a drainage implant for a glaucoma patient, and to a method for using such a device.

BACKGROUND OF THE INVENTION

Glaucoma is a common cause of blindness or visual impairment throughout the world, affecting about 1 person in 40 at some point in their life to a varying degree. In glaucoma, the fluid drainage pathways from the eye become restricted or damaged. As a result, fluid pressure within the eye (the intra-ocular fluid pressure, IOP) rises and the optic nerve is damaged by the raised fluid pressure.

Medical treatment, typically by the application of eye drops containing drugs which either decrease intraocular fluid production or increase outflow, requires lifelong compliance which is only infrequently attained in practice. Medical treatment is often only partially successful in retarding disease progression, with continued optic nerve damage and visual field loss.

The alternative is glaucoma drainage or filtration surgery (GFS), in which a drainage channel (the GFS channel or fistula) is created through the wall of the sclerocorneal junction by a laser beam or other means to connect the anterior chamber (the fluid space within the eyeball in front of the pupil) directly with the subconjunctival space (the space beneath the membrane covering the white of the eye). The GFS channel thus provides a route through which fluid can drain from the interior of the eye to the subconjunctival space. Successful GFS has been shown to provide better quality IOP control and better protection from disease progression than medical treatment in glaucoma.

However, problems arise in controlling drainage of fluid after GFS. Excessive drainage leading to hypotony (IOP less than a safe minimum level, which is about 5 mmHg) can result in a number of sight threatening complications including suprachoroidal haemorrhage and hypotony maculopathy. On the other hand, inadequate drainage with an insufficient IOP reduction (more than 15 mmHg) increases the risk of continued optic nerve damage. The IOP should ideally stay within the safe range (ie 5–15 mmHg) after GFS avoiding both early hypotony and later inadequate drainage. No current GFS technique achieves this goal consistently and complications after GFS remain common.

After GFS, limited subconjunctival scarring tends to form a partial seal around the area of the surgical drainage outlet (bleb formation). This process adds an additional flow resistance element (bleb resistance) and results in an increase in IOP from the initial postoperative level, which continues until postoperative inflammation subsides and the wound healing response is complete. This postoperative wound healing response varies considerably between individuals and is often modulated with anti-scarring treatments such as 5-fluorouracil and mitomycin C. IOP thus stabilises at a variable final level. To achieve the lowest safe final IOP level safely, current GFS techniques attempt to build a resistance element into the GFS channel (guarding, or fistular resistance) to protect from early overdrainage which can ideally be retained if bleb resistance is low, or abolished if bleb resistance is adequate to prevent late hypotony.

Currently preferred surgical practice, trabeculectomy with releasable sutures, uses a partial thickness scleral flap secured by one or more sutures tied in a slip knot to provide a trap-door type covering over the drainage passage through the wall of the eye. Guarding provided by this scleral flap, and hence the initial postoperative IOP level, is inconsistent. Also, early suture release often results in hypotony, whereas scarring beneath the scleral flap tends to make later suture release ineffective in abolishing fistular resistance.

SUMMARY OF PRIOR ART

In another form of GFS, a glaucoma filtration implant (GFI) is inserted into the GFS channel. Current GFIs are commonly associated with excessive drainage and early postoperative hypotony. This results from either poor control over flow through the GFI, uncontrolled external leakage of fluid between the GFI and the walls of the GFS channel into which it is inserted, or both poor internal flow control and external leakage.

A variety of GFIs are in clinical use. The first device to be made clinically available, and which is probably the device preferred by most ophthalmic surgeons, is the Molteno implant. This consists of a flexible silicone rubber drainage tube, one end of which is introduced into the anterior chamber and the other end of which opens onto a plate shaped explant formed of moulded polypropylene, which is secured to the sclera 5–6 mm supertemporal from the limbus through a fornix-based conjunctival flap. The open side of the plate faces outwards. The original Molteno implant had no internal mechanism which created flow resistance. The long term flow resistance is created by the bleb which forms by wound healing mechanisms over the explant. In order to avoid postoperative hypotony, it was necessary either to install the implant in two stages (the tube being inserted in the second stage) or with the tube temporarily ligated, for instance using a biodegradable or laser ablatable suture.

The flow rate following implantation to the original Molteno device depends primarily upon the rate at which the fluid can drain from the plate explant, which in turn depends upon the wound healing reaction. Whilst some control is available by providing implants having different plate areas, this is inadequate in many circumstances. Improvements in the design include the Molteno dual ridge device which has a v-shaped ridge on the plate adjacent to the tube plate junction dividing the available spacing in the concave side of the plate into a small anti-chamber (having a volume of approximately 15 microliters) and a larger main chamber. In use aqueous humour must percolate between the overlying Tenon capsule and the ridge to fill the larger main chamber, from which it can filter. Whilst this provides some improvement to control of flow resistance, this is still inadequate in some circumstances.

Another variation on the original Molteno device is the Baerveldt device. This again consists of a plate shaped explant and a tube opening onto the concave side of the plate, but is implanted in apposition to the sclera rather than the conjunctiva (as for the Molteno implant).

One problem with both the original and dual ridge Molteno devices and the Baerveldt device is that the flow resistance is very dependent upon suture tension. For all of the devices the eventual IOP can be too low for safety and all are subject to progressive fibrous obliteration by continued subconjunctival wound healing processes after surgery, which may result in eventual filtration failure. All of the above devices depend upon bleb resistance for flow resistance and require implantation by two stages or use of removable or biodegradable ligatures.

Devices are available which incorporate valves in the flow passage to avoid immediate postoperative hypotony and the need for a two stage surgical procedure or the use of ligatures. Two such devices are in clinical use, the Krupin device which uses a slit valve and the Ahmed device which uses a venturi type valve. One problem with at least the Krupin device is that of hysteresis, that is that the valve closes at a lower pressure than it opens. In addition both devices have been shown not to open and close as claimed in vivo (Prata et al, Ophthalmology (1995) 102, 894–904). For both these devices therefore the "valves" behave only as flow restriction devices, with the main contribution to resistance to flow being bleb formation. Both these devices are subject to eventual fibrous obliteration and filtration failure.

In WO-A-91/12046 a plate type device has an elongated tube having an elliptical external section. This is said to reduce leakage of aqueous humour by providing a closer fit between individual lamellae in the sclerotic layer, between which the tube is implanted. The diameter of the internal lumen through the tube is selected to provide some resistance to flow. The diameter/length combinations to provide appropriate resistance to flow are disclosed to lie in the range 10 to 20 mm for the length and 0.15 to 0.21 mm for the diameter.

A problem common to all the above GFIs is that the relatively rigid plates lead to transmitted movement along the respective tubes in association with eye movements. This can lead to mechanical attrition of corneal endothelial cells, erosion of the sclera and implant extrusion. All of the devices require a relatively large conjunctival wound to accommodate the external plate element. The large plate element is intended to prevent fibrous obliteration of the subconjunctival filtration area which could potentially be avoided with the increasing availability of anti-wound healing drugs.

It has also been suggested to provide GFIs with other means of controlling internal flow resistance, rather than rely upon bleb resistance alone. One type of device in clinical use is the OptiMed, which consists of a rubber tube connected to a rigid explant formed of polymethylmethacrylate in the form of microtubules each having internal diameter of around 60 micrometers, through which aqueous humour flows from the anterior chamber into the periocular space.

One problem with most of the devices described above is that immediately after surgery there is a significant amount of leakage around the outside of a circular section drainage tube. One reason for this is that a circular section tube is inserted through a slit incision and there is inevitably a space between the outside of the tube and the slit through which leakage can take place. Another reason is that the tube must have adequate hardness to prevent its collapse once implanted. The surface of such materials tends to be relatively non-deformable, so that the external circumference of the device does not deform to fit the channel made by the slit incision.

The present invention solves the problem of external leakage around a device having a conduit for fluid and which is inserted into the eye to allow flow of fluid into and/or out of the eye.

Suson and Kalenak, at the Annual Meeting of the Association for Research in Vision and Ophthalmology 1996, described a glaucoma implant in which the flow rate through the device could be selectively increased by laser drilling increasing numbers of microscopic holes in the wall of a silastic tube implant in the portion extending into the anterior chamber. One problem with this method is that a large amount of power may be required to penetrate silicone rubber materials.

In U.S. Pat. No. 5,433,701 a glaucoma filtration implant comprises a widened body section and a narrower drainage section comprising laser ablatable flow restrictors in channels. The drainage tube has an oblong external periphery having a generally rectangular shape, the longer sides of which are substantially rectilinear. The peripheral shape of this tube is likely to allow excessive leakage around the outside of the tube immediately after implantation through a slit incision.

The surgical incision into which a glaucoma implant is inserted is a slit. Existing devices use tubes with circular or rectangular external section to be located in the incision. Devices which are fully constricted, for instance by a biodegradable or laser ablatable suture, must allow for some leakage around the external surface of the device immediately after surgery for initial reduction in IOP.

DESCRIPTION OF THE INVENTION

The present inventor determines that it would be desirable for a device to be provided which allows a predetermined flow rate of intraocular fluid through the device whilst minimising flow through the incision around the outside of the device and preferably allows for adjustment of the flow rate after implantation.

A new device according to the invention for positioning in a slit aperture in the eye of a human or animal patient for relieving glaucoma comprises an elongate body section, interior and exterior end sections at the respective interior and exterior ends of the body section, and at least one lumen extending through the body between the interior and exterior ends thereof, and the exterior end section preferably has a channel one end of which has a mouth which opens to the outside of the device (i.e. in said other cavity) and the other end of which is in fluid communication with at least one of the said at least one lumen, the interior end section has a passageway one end of which has a mouth opening into the internal chamber of the device and the other end of which is in fluid communication with the at least one of the said at least lumen whereby the device has a conduit for fluid flowing from the internal chamber of the eye which conduit extends through the passageway, through the lumen and through the channel and out through the said mouth, the body section being adapted for positioning in a channel in the wall of the eye, the interior end section being adapted for being located so that it extends into an internal chamber of the eye and the exterior end section being adapted for being located in use in another cavity, in which the body section has a cross section perpendicular to its axis the external perimeter of which is oblong having a longest diameter and a shortest diameter and forms a substantially continuous convex curve. The curve optionally includes one or more straight sections each forming an angle in the range 15 to 45° to the longest diameter and generally intersecting the longest diameter, and/or straight sections substantially parallel to the longest diameter.

The section perpendicular to the axis of the body section should have a circumference which has no inflection points i.e. is at no point concave, but rather is preferably convex around the entire circumference.

In the present specification the term oblong is used to refer to a shape which is longer than it is broad. Preferably the long diameter (i.e. through the axis) will be perpendicular to the shortest diameter, and the shape will be symmetrical about the longest and shortest diameter, there will be only one position where the diameter is greatest and only one position where the diameter is least and the diameter (i.e. through the axis) should preferably increase continuously from its minimum to its maximum. The shape is comparable with an axial section through a biconvex lens. It is possible for the shape of the section to include one or more substantially straight sections which form an angle of less than 45° to the long diameter, preferably less than 30°, more preferably less than 25°. Preferably, however, the shape is oval or elliptical, i.e. a conical section having the shape of a section through a circular cylindrical body said section being other than perpendicular to the axis.

Another preferred shape consists of two arcs each of circles of substantially equal radii (less than $\pi/2$ radians) joined at their end points by curves (e.g. circular) of small radius of curvature. Such a shape is generally based on a curve, with the intersection points being somewhat rounded. The radius of curvature of the end points is for instance less than half the radius of curvature of the arcs preferably less than 0.25 of the radius. Preferably the ratio of the greatest diameter to that of the smallest diameter is in the range (3–1.2):1, preferably in the range (2.5–1.5):1.

Preferably the shape is the same along the body section. For some embodiments it is preferred that the cross-section has the same dimensions along the body section, i.e. the body section is cylindrical. For other embodiments, it may be preferred for the body section to have a taper, for instance widening towards the interior end section to assist retention of the device in situ. In a particularly preferred embodiment of the device the taper is of the smallest diameter but not the longest, which takes into account of the fact that inward retaining pressure is exerted by the cut faces of as lit incision.

The device is inserted into an incision formed as a slit with the cross-section's greatest diameter aligned with the slit. The external profile of the device ensures that the tissues at the incision bear directly against the external wall of the implant around substantially the entire circumference of the implant. This minimises flow of fluid through the incision around the external wall of the implant.

To provide a further reduction in the flow of fluid through the incision around the outside of the implant, it is preferred for the body section along at least part of its length to be formed of an external layer at the external surface of the body section and at least one internal layer, in which the external layer is resilient and has a relatively low hardness, whilst the internal layer is formed of a material having a higher hardness. The use of a softer material at the surface of the device allows for the surface to deform to conform to the tissue at the incision, thereby minimising any gap between the device and the tissue. The use of a material having a higher hardness for an internal layer allows the or each lumen, which will be surrounded by the harder layer, to remain open and be unaffected upon imposition of an external force on the outer surface of the implant. This allows maintenance of fluid flow at a predetermined flow rate through the conduit. Preferably it is the interior end section at least of the implant which is provided with the layers of different relative hardness.

In this embodiment of the invention the hardness of the respective materials refers to the hardness under conditions of use, in terms of surrounding/imbued liquid environment and temperature.

Alternatively the device may be formed of a relatively soft material to allow local deformation at the external surface but be provided with reinforcement to prevent or minimise deformation at the internal wall that could occlude the lumen. Additionally or alternatively the outer surface of the body section of the device could be formed of a gel material which swells after insertion of the device in an incision, the extent of swelling being dependent upon the pressure exerted on the surface of the material by the internal surface of the slit incision.

The materials from which the device is formed should be selected for their appropriate hardness as well as biocompatibility and ease of use for manufacture of the device. In the present specification the term "biocompatible" means inert to tissues and liquids which the component defined thereby may contact in use. The term thus indicates that the component will not generate an inflammation or wound healing reaction in the tissue. Although it may often be desirable for the biocompatible surfaces to be selected such that there is minimal tissue adhesion to the surfaces, there may be advantages in selecting a surface to which cells do adhere, as this may minimise leakage around the outside of the device. Materials which contact biological fluids and which are insufficiently biocompatible themselves, may be subjected to treatments to improve their biocompatibility, for instance by being blended with biocompatible materials, alternatively they may be chemically altered or a preformed device may be surface treated or coated with a biocompatible material.

Suitable materials for forming the basis of the device are elastomeric in nature, and can be adapted to provide the necessary softness for use as the outer layer of a multilayer device and the relatively harder internal layer which protects the lumen. Suitable elastomers are, for instance, silicones or polyurethanes. Alternatively suitable materials, especially which swell in use may be hydrogels.

Where the materials are thermoplastic, they may be shaped by melt processing techniques. For nonthermoplastic materials, for instance hydrogels or other cross-linked materials, the device may be formed by polymerising or crosslinking a liquid starting material in a mould. The bulk formed product may form the device itself or may form a precursor which is subjected to subsequent shaping steps such as lathe cutting, drilling etc. Silicone based devices and or cross-linked polyacrylates may be made by such moulding techniques Polyurethanes may be made by melt blending techniques.

Where the material of the external surface is of a different type to the relatively hard internal material through which the or each lumen is formed, a precursor for forming the relatively hard portion may be preformed, for instance by melt processing techniques or by polymerisation or crosslinking of liquid starting materials in a mould. The preformed hard portion may subsequently have the relatively soft outer layer formed onto it by coating it with a liquid precursor of the soft material, e.g. a solution of preformed polymer in a solvent, or a polymerisable or cross-linkable liquid which forms the soft material upon curing. The coating may take place in multiple stages to build up an adequate thickness for the surface layer to be sufficiently deformable in use. Alternatively the preformed hard portion may be placed in a mould with liquid precursor for the softer portion which is then polymerised or crosslinked in the mould in the presence of and around the preform. A melt processable softer material may be extruded onto a preformed harder component or, where both materials are melt processable they may be coextruded in the desired shape.

Suitable biocompatible polyurethanes are described in patent publications U.S. Pat. Nos. 4,689,386, 5,453,467 and WO-A-95/05408. Hydrogel materials are described in EP-A-0555295. The hardness (in use) of a hydrogel material may be controlled by the choice and relative quantities of monomers and control of the degree of swelling by adjustment of the degree of crosslinking and/or by incorporating of pore forming components during polymerisation, whereby eventual water content can be controlled.

Where the device is preformed, of materials which are desired to have increased biocompatibility, such devices may be surface treated, so as to introduce improved biocompatibility at the surface. Examples of surface treatment processes to provide improved biocompatibility are described in EP-A-0157469, EP-A-0518959, EP-A-0601041 and EP-A-0556216. Coating methods, in which a polymer coating is provided at the surface are described in EP-A-0032622, EP-A-0641226, EP-A-0593561 and EP-A-0625915.

The above mentioned patent specifications describing biocompatible materials are all primarily concerned with the introduction of phosphoryl choline groups and other zwitterionic groups at the surface to improve the biocompatibility. The use of analogues of phosphoryl choline is described in WO-A-94/16748 and WO-A-95/20407.

The device of the invention may be a sleeve which is used to surround a phakoemulsification tip and/or a device for introducing and removing liquid during a phakoemulsification procedure and/or a device for manipulating fragments of a lens during or following the phakoemulsification procedure. Alternatively the device may be a sleeve for an irrigator for use during retinal surgery. The main utility of the invention is for a device which includes at least one lumen for flow of liquid, and of which occlusion should be prevented whilst minimising escape of liquid around the outside of the device through the slit incision.

The invention is of particular application in the relief of internal pressure notably in surgery to the eye to relieve internal fluid pressure in the treatment of glaucoma. For convenience, the invention will be described hereinafter in terms of the use of the device to regulate the IOP in a human eye following GFS.

In the use of the glaucoma filtration device of the invention, the resistance to fluid flow will increase after surgery following formation of a bleb. The device is preferably formed of materials which minimise the foreign body type inflammation and wound healing processes in the tissue following surgery. It is preferable for the device not to comprise a plate type drainage surface nor other large component. It is believed that the function of such components in prior art glaucoma filtration implants to maintain a high surface area for drainage of fluid despite formation of scar tissue, will not arise for the present, biocompatible device. External flow is minimised by the external shape of the body section of the device. The lumen allows a low level of liquid flow from the eye through a lumen in the body section and out to the outside of the device.

The implant can be of any suitable length, depending upon whether the tube is to drain fluid to the anterior conjunctiva or whether it is to extend in the sub conjunctival space further posteriorly, for example where the anterior conjunctiva is too scarred or where it is expected that hard contact lens wearing will be desired after surgery. Where there is too much scarring for drainage to the sclera the device may be implanted to drain to the supra-choroidal space, in which case the length may be approximately the same as for posterior filtration. Where the device of the invention is to be used for drainage from the anterior chamber into the anterior subconjunctival space, case the total length of the device will be from about 1 to 7 mm, typically 2 to 6 mm, preferably 3.5 to 5.5 mm. A device for posterior or choroidal filtration will have a total length of about 2 to 20 mm, preferably about 3 to 15 mm for instance 5 to 10 mm.

The lumen(s) is (are) preferably sized so that it imparts no significant flow resistance to the drainage of fluid along most of its length. The lumen, or the interior end section passageway or the exterior end section channel preferably has a flow resistance element. For a single microtube resistance element, the calculation of the internal diameter of the channel is as follows:

The aqueous flow rate (Q) is 2.75 (±0.63) $\mu$l/min, or approximately $4.58 \times 10^{-11}$ m$^3$/sec.

Aqueous viscosity (n)=$10^{-3}$ Nsec/m$^2$.

The pressure drop (pd) across a tube given by Poiseuille's formula is:

$$pd = 128 n.l.Q/\pi d^4 \text{ N/m}^2$$

or $$pd = 128 n.l.Q/136\pi d^4 \text{ mmHg}$$

(where 1 mmHg=136 N/m$^2$)

where l=tube length and d=tube diameter.

For a tubular resistance element within a glaucoma filtration implant therefore the relationship between pressure drop (pd), tube length ($l^1$) in $\mu$m, and tube diameter ($d^1$) is $\mu$m is given by:

$$pd = 1.372 \times l^1 \times 10^{-20}/(d^1 \times 10^{-6})^4 \text{ mmHg}$$

The target pressure range on Day 1 after glaucoma filtration surgery is 5–15 mmHg. As examples, for the conduit a portion of predetermined length a reduced diameter to act as a flow resistance element has (the rest of the lumen imparting less or no significant resistance to flow by having a diameter greater than about 50 $\mu$m). For a resistance element of length 300 $\mu$m:

$$d^1 = 30 \ \mu m \ pd = 5 \ \text{mmHg}$$

$$d^1 = 25 \ \mu m \ pd = 10.5 \ \text{mmHg}$$

$$d^1 = 23 \ \mu m \ pd = 14.7 \ \text{mmHg}$$

The formula can be used to calculate a range of suitable length/diameter combinations for a range of suitable flow rates. The resistance element preferably has a length in the range 5000 to 100 $\mu$m, preferably in the range 2000 to 200 $\mu$m, more preferably no more than 1000 $\mu$m. We have established that it is practically possible to drill a hole in a material of thickness up to at least 2000 $\mu$m of small enough diameter to generate a resistance element to achieve pressure differences in the desired range. We have furthermore established experimentally that the measured pressure difference correlates well to the value calculated by Pouseuille's formula, above. Preferably a flow resistance element in the conduit has a length l $\mu$m and diameter d $\mu$m meeting the requirement $$100 \leq l \leq 5000,$$

$$5 \leq d \leq 100$$

$$2 \times 10^{-4} \leq l/d^4 \leq 2.5 \times 10^{-3}$$

Preferably d is at least 10 $\mu$m, more preferably at least 15 $\mu$m, most preferably at least 20 $\mu$m. Preferably $l/d^4$ is at least $3.6 \times 10^{-4}$ and is less than $1.8 \times 10^{-3}$.

Despite the improved biocompatibility of the present product and improvements in pharmaceuticals for controlling wound healing, there will almost inevitably be a reduction in fluid flow after limited wound healing associated with surgery has taken place. Where this reduction could be excessive leading to relapse and post-surgical increase in IOL, it is preferred for there to be a removable flow inhibitor located in a passageway in the interior end section of the device leading from a lumen extending through the body and which opens to the outside of the device. The flow inhibitor should preferably be formed of a laser ablatable material and is located at the internal end section of the device so that a laser can be directed through the cornea which is transparent to visible and near infra-red laser light. Initial flow through the device should be sufficient to establish an initial post-operative IOP in the safe range (5 to 15 mmHg). The flow restrictor may completely occludes the conduit, effectively preventing passage of liquid from the eye to the outside of the device i.e. there is no permanently open resistance element. It is usually desired that there should be some low level of liquid flowing through the device immediately after surgery. There is preferably additionally a flow restriction element as described above.

The internal cross-sectional area of the parts of the conduit formed by the lumen, the channel through the exterior and the passageway through the interior end other than any resistance element is preferably equivalent to a circular cross-section having a diameter at least 250 µm, preferably at least 300 µm. The optimal internal diameter can be determined from a knowledge of the material of construction of the implant, the property of the surface of the lumen and the viscosity of the optic fluid and the desired IOP pressure which is to be maintained in the eye after any flow restricting means have been partly or wholly removed and by experiment.

Alternatively the lumen may have a length and a diameter such that it does restrict flow, that is having constant a diameter in the range 10 to 250 µm along the entire length. For such a device the lumen may include several microtube elements such as are used in the OptiMed device (op. cit.).

The implant is preferably provided with means whereby it can be located and retained in the GFS channel. This can take the form of a radially outwardly extending flange or shoulder or a series of radial fingers at the exterior end of the implant which butt against the outer surface of the wall of the eye as the implant is seated into the GFS channel so as to minimise the risk of over insertion of the tube. It is preferred additionally or alternatively to provide the interior end section of the implant with means whereby the tube can be retained in the GFS channel so as to prevent ejection (extrusion) of the tube from the channel. Thus, it is preferred to provide the interior end section with a saw tooth or other radial projection which deploys laterally once the interior end section of implant projects beyond the inner face of the wall of the eye.

In a preferred embodiment, the interior end section of the tube is provided with a deformable radial flange or a series of deformable radial fingers. Where the device is inserted from outside (ab externo), this flange or fingers may deform to lie substantially parallel to the wall of the body section as the implant is inserted into the GFS channel, but which splay radially once the interior end section extends beyond the inner face of the wall of the eye and the body section is in the GFS channel. A continuous internal flange also assists in preventing uncontrolled leakage of fluid between the outer wall of the implant and the inner wall of the GFS channel.

A flange (at the interior or exterior end) may be formed as a flat annulus which is coaxial with the body section. Preferably, however, so that the flange conforms with the internal wall of the anterior chamber or fits in the subconjunctival space, the annulus has an axis which is at an angle to the axis of the body section, preferably crossing the axis of the body section in the centre of the annulus. The angle between the axes is preferably in the range 15 to 45°, more preferably around 30°.

To aid delivery of a device having a flange or similar externally projecting members at the interior or exterior end section, and/or to improve the retention of the device in place in use, the respective end section may have a reduced outer diameter as compared to the body section. The external wall of the end section may have a conical surface or be otherwise tapered to the junction with the flange. It may, in addition, be desirable for the opposite end section which does not have a flange or parts or all of the body section to be tapered, for instance the external wall may have a conical surface for instance to assist insertion.

As stated above, the implant of the invention is preferably provided with a flow inhibitor means adapted to be varied so as to regulate the flow of fluid through the conduit according to the proportion of the cross-sectional area and/or axial length of the flow restriction means which remains in the passageway. By forming the flow inhibitor so that it can be removed to achieve the desired variation in flow restriction, it is possible to select the dimensions of the lumen, channel and passageway (including any resistance means) and of the flow inhibitor means such that the desired final IOP after bleb formation corresponds to the complete removal of the flow inhibitor means. The implant may impose little or no flow restriction on the drainage of fluid from the interior of the eye in which event a flow resistance means is unnecessary. However some resistance to flow to maintain an IOL (pressure difference) at least 5 mm Hg is generally needed.

The passageway of the interior end section can be partially closed by a transverse reticulate, foraminous or porous membrane at or adjacent one end of the tube as flow inhibitor to provide a limited initial flow through the implant so as to retain a high IOP immediately after the implant has been inserted into the GFS channel. This membrane can then be cut away or punctured by a needle, a conventional ophthalmic laser or by any other suitable means to reduce the flow inhibition. This allows the surgeon to achieve a selected reduction in the IOP once the scar or bleb formation has stabilised so as to prevent an unacceptable rise in the IOP thereafter. In place of a transverse membrane, the implant can be provided with a porous or fitted plug which is cut away as with the membrane.

The flow inhibitor means may be secured across the mouth of the passageway of the interior end section of the implant. However, the flow inhibitor means can extend axially for part or all of the passageway in the interior end section or even into the lumen of the body section, as when a foamed plastic or a ceramic frit insert is secured within the tube.

The flow inhibitor means can form an integral part of the implant, for example as when a transverse membrane is heat sealed to the lip of the interior end section of the implant; or can be formed as a separate insert member which is secured within the implant. Where this insert member is not fixed in the passageway during manufacture, but rather by the surgeon, a variety of alternative insert members may be provided with a device for providing different degrees of inhibition of flow.

The flow inhibitor need not be made from the same material as the other components of the implant, provided that it is physiologically acceptable and can readily be removed by simple means. However, to facilitate subsequent removal of the flow inhibitor means, it is preferred that the flow inhibitor means be made from a material which can be readily ablated or cut away by a laser, thus simplifying removal of part of all of the flow inhibitor in one or more stages as the IOP rises and the flow through the implant is to be increased. The flow inhibitor can be provided by a flexible or rigid gel or solid material or thermally degradable foamed plastic infill to the tube and the flow inhibition of the infill varied by destruction of the material eg by collapsing the foam, using a laser beam to form one or more axial bores through the length of the infill, or by eroding the full cross-sectional area of the infill progressively so as to reduce the axial length of the infill. It may be possible to incorporate a pigment or other chromophore where a thermal laser is used to enhance the heat absorption properties of the flow inhibitor and thus make it more susceptible to thermal destruction by the laser than the adjoining clear tubular wall of the body section and/or interior end section of the implant.

Since, upon laser ablation of the flow inhibitor new surfaces will be formed which will be in contacting use with intraocular fluid, it is preferred for the material of the flow inhibitor to be formed of biocompatible material. Thus if any of the material of the flow inhibitor remains as part of the implant, the contact of intraocular fluid with the remaining portions will not cause any reaction and hence minimise disruption of the tissue and healing process. Preferably therefore the flow inhibitor is formed of a biocompatible material, preferably one which is rendered biocompatible by the incorporation of phosphoryl choline groups. Materials which are elastomeric and which do not swell in situ once implanted, such as silicone rubbers, tend not to be easily ablated with a laser. The material may be formed of, for instance, polyesters, polyakenes, or poly(alk)acrylic compounds, such as poly(alk)acrylate esters of lower alkanols or derivatives, especially polymers of methyl-methacrylate and co-monomers containing phosphoryl-choline groups.

The flow inhibitor may be adapted so as not to occlude the channel completely, but rather to allow a low level of flow. Thus the immediate post-operative level of flow may be through the flow inhibitor. In that case the flow inhibitor properties of the flow inhibitor can be selected in known manner. The calculation will have regard to the initial IOP which is to be achieved, the viscosity of the fluid to drain through the tube (which can be assumed to be substantially the same as water, in practice) and the dimensions of the implant, the lumen and the channel in the exterior end section and the passageway and any flow resistance means thereof and the size and character of the flow inhibitor using the calculation set out above relying on Poiseuille's formula. The formula may allow an estimation of the effective hydraulic diameter where the flow inhibitor has pores, weave apertures or passageways and the parameters can be adjusted after experiment.

Having inserted the implant of the invention, the flow inhibitor achieves an initial resistance to flow through the device, thus preventing excessively low initial IOP. As the scar formation around the exterior end section of the implant occurs, the total flow rate decreases and the IOP rises. The flow inhibitor within the implant can then be removed or modified so as to permit increased flow of fluid through the implant to compensate for the development of the scar tissue or bleb formation and thus regulate the IOP. Removal of the flow inhibitor usually occurs once the scar or bleb formation has stabilised. However, the removal of the flow inhibitor can be carried out during this phase of the post surgical procedure where excessive IOP increase occurs. As indicated above, the reduction in flow inhibition can be achieved by increasing the transverse area of any pores or other passages extending axially through the flow inhibitor; by reducing the axial length of the flow inhibitor means and hence its flow inhibition; or by a combination of both. It is also within the scope of the present invention to increase the number of axial passages through the inhibitor, for example by using a laser beam to form new axial passages through the flow inhibitor (which may then create a flow resistance element) in addition to or as an alternative to increasing the effective diameter of existing passages. It will be appreciated that the flow inhibition of the flow inhibitor can be altered progressively in a series of steps so as to provide a measure of control over the final flow rate, thus compensating for unexpected variations in the IOP stabilisation following the GFS surgery. Typically, as indicated above, the implant including any resistance means and the flow inhibitor are sized so that the whole of the flow inhibitor is removed to remove substantially all resistance to flow, at which point the desired final IOP is achieved. Adequate IOP's in this case are achieved by bleb formation. This is to be contrasted with the above-described OptiMed implant where the residual resistance to flow is often significant.

The invention also provides a method for regulating the flow of fluid from an internal chamber of the eye, which method comprises forming a fluid escape channel from the internal chamber, as a slit, inserting a device of the invention into the channel such that the greatest diameter is aligned with the slit and allowing fluid to flow from the internal chamber of the eye through the lumen and out through the exterior end of the device. Preferably the method includes the step of selective reduction of the flow restrictive properties of flow restrictive means of the implant. Preferably internal chamber of the eye is the anterior chamber, the escape channel is a channel formed by the GFS surgical technique, and the flow of fluid through the device is varied to achieve a desired IOP within the eye.

DESCRIPTION OF THE DRAWINGS

In the method of the invention, it is preferred to use a laser in removing the flow restriction means.

The invention is further illustrated in the accompanying drawings in which.

DESCRIPTION OF PREFERRED EMBODIMENTS

Figure 1:
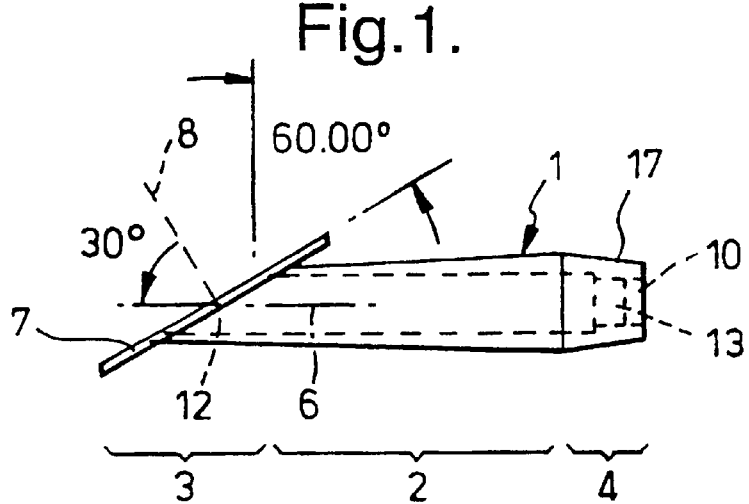
FIG. 1 is a side view of an embodiment of the glaucoma filtration implant of the present invention, which is adapted for anterior filtration.

A glaucoma filtration implant 1 for anterior filtration comprises a body section 2, an interior end section 4 and an exterior end section 3. The body section 2 is tapered along its length at the upper and lower portions of the circumference, reducing in diameter towards the exterior end section 3. Interior end section 4 also has a taper.

Exterior section 3 comprises a flange 7 which is a circular washer-shaped annulus, the axis 8 of which is at an angle of 30° to the axis 6 of the body section 2. The device is about 3 mm in total length, the flange being about 1.75 mm in diameter and about 0.1 mm thick.

The device comprises a lumen 9 through the centre section, coaxial with the body section 2. The lumen 9 is in fluid communication with passageway 10 in the back wall 17 of the interior end section 4 of the implant. Exterior end section 3 includes a channel 12 in fluid communication with the lumen 9. In this embodiment, lumen 9 and channel 12 have the same diameter as one another and are the same shape in cross section that is oval with a larger diameter of about 0.6 mm and a smaller diameter of about 0.45 mm. The passageway 10 is conveniently circular and has a smaller diameter than the lumen 9, in this embodiment about 0.3 mm.

Located in the passageway 10 is a plug 13 forming a flow inhibitor which substantially prevents flow of intraocular fluid therethrough, thereby blocking passage of intraocular fluid into the passageway 10 and through the lumen. The plug 13 is formed of a laser ablatable polymer material, for instance a copolymer of methylmethacrylate and (2-methacryloyloxyethyl)-trimethylammonium)ethyl phosphate inner salt. Thus, this embodiment it is formed of a material which is biocompatible throughout its volume. Upon ablation by a laser as used in ophthalmic surgery, some or all of the material forming plug 13 will be removed from the passageway 10. Where less than all the material is removed by the laser, some of the material will be left within the passageway, exposing surfaces of the material to intraocular fluid. Where the material is made from the phophoryl choline-group containing polymer, these surfaces will be biocompatible and will resist deposition of protein and other components of the intraocular fluid produced immediately after surgery. Upon ablation of the plug 13, the passageway 10 is open, allowing passage of intraocular fluid through the conduit formed by passageway 10, lumen 9 and channel 8 out through the mouth 14 at the exterior end of the exterior end section.

Figure 2:
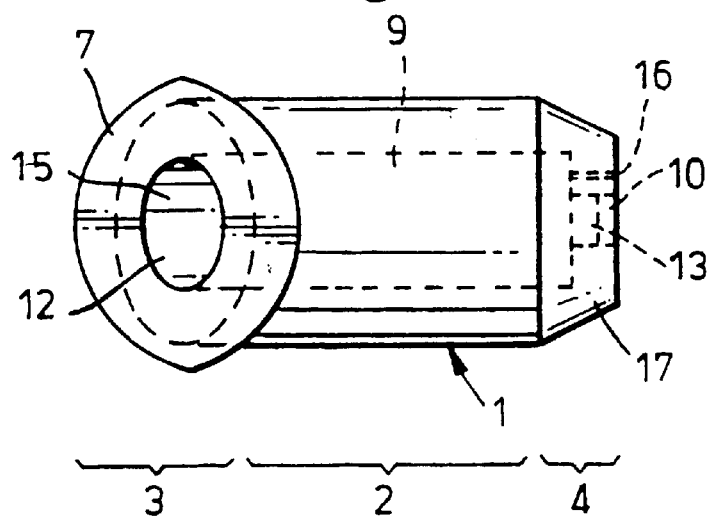
FIG. 2 is a view from the top of the device shown in FIG. 1.

As shown in FIG. 2, the flange 7 forming part of the exterior end section 3 is annular in shape having an aperture 15 in its centre. Aperture 15 surrounds the exit of passageway 12. Since the passageway 12 is oval in cross section (perpendicular to the main axis 6 of the implant), the aperture 15 is oval in horizontal projection.

Figure 3:
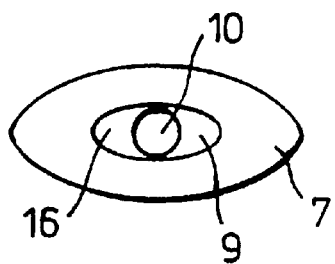
FIG. 3 is a view from the right hand end of the embodiment shown in FIG. 1.
Figure 4:
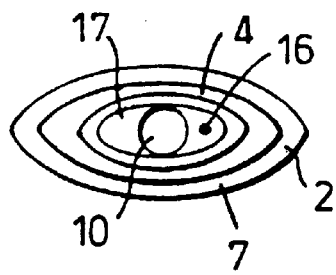
FIG. 4 is an end on view from the lefthand end of the embodiment shown in FIG. 1.

As can be seen in FIGS. 2 to 4, the external periphery of the body section 2 of the implant is not circular, but rather has a greater diameter in the direction into the page in FIG. 1 (along the vertical axis in FIG. 2), than in the vertical direction in FIG. 1 (into the page in FIG. 2). In this embodiment, the longer diameter of the section through the central section 2 is 1.5 mm, whilst the smaller diameter is from 0.5 at the exterior end to 0.6 mm at the interior end. The horizontal projection of the flange 7 is of substantially the same shape as the vertical section through the body section 2 of the device. The largest diameter of the flange 7, which is in the horizontal line through the axis, is 2.0 mm. As shown in FIGS. 2, 3 and 4, there is also provided a bore 16 acting as a flow resistance element extending through the wall 17 of the interior end section 4 into the lumen 9. This bore is in fluid communication with intraocular fluid in the anterior chamber of the eye in use and allows unguarded passage of intraocular fluid to the filtration area. The bore 16 has a diameter selected so as to allow adequate reduction in IOP immediately after surgery and before wound healing and bleb-formation commence without allowing the IOP to drop to a dangerously low level. In the present embodiment the wall 17 is about 300 μm thick and the diameter of the bore 16 is 0.025 mm.

The device illustrated may be formed, for instance by moulding in a moulding operation to the desired shape. The lumen, channel and passageway may be formed by including in the mould a rod of material which is insoluble in the liquid mixture used to form the polymer part of the body section surrounding the lumen, channel and passageway but which is soluble in a non-solvent for the polymer. Alternatively the lumen, passageway and channel may be formed after the moulding operation, for instance by the use of a laser. Bore 16 is so narrow that it is preferably formed by the use of a laser although it may be possible to form it by blasting with small hard crystals such as salt, in a fluid vehicle such as air. Suitable moulding processes include thermoforming a thermoplastic material and compression or injection moulding, crosslinking a liquid prepolymer containing polymerisation mixture in a mould or polymerising a liquid monomer mix in a mould. Suitable prepolymers for crosslinking in a mould are silicone type polymers. Suitable thermoplastics for thermoforming include polypropylene. Liquid monomer mixtures which can be polymerised in a mould are acrylic type polymers, especially monomer mixes suitable for forming relatively soft crosslinked polymers.

Preferably the device is made from a relatively soft external layer and a relatively hard internal layer surrounding the lumen 9, passageway 10 and channel 12. The internal layer may thus have an oval section cylindrical passageway and have an external wall having an oval periphery or a circular cylindrical periphery. Preferred methods of forming two layer or multilayer devices are coextrusion or sequential moulding steps. It may be convenient to use a combination of methods for forming the different layers.

Figure 5A:
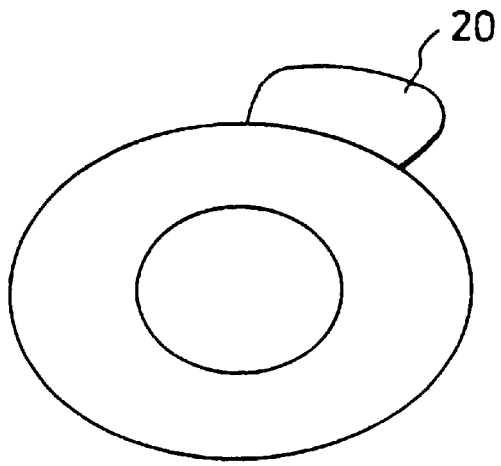
FIGS. 5a–d are schematic diagrams showing the steps in the surgical procedure to implant the device of FIG. 1.
Figure 5B:
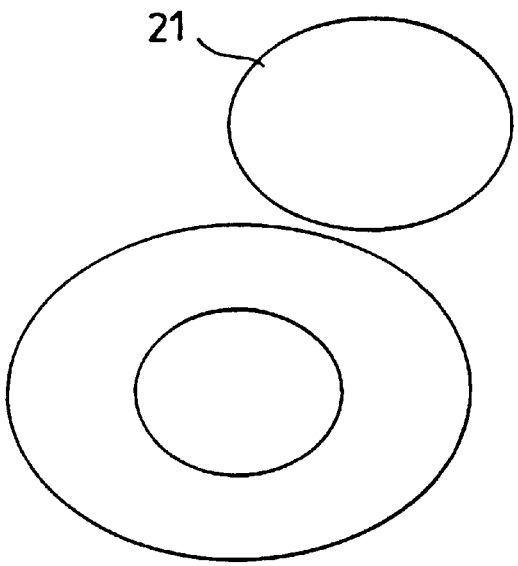
Figure 5C:
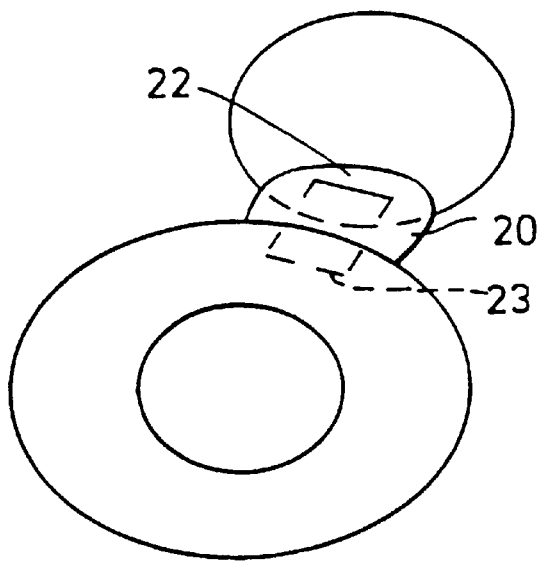
Figure 5D:
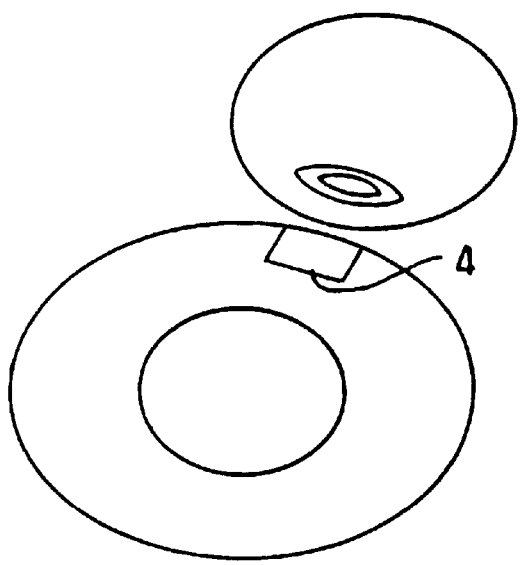
Figure 6:
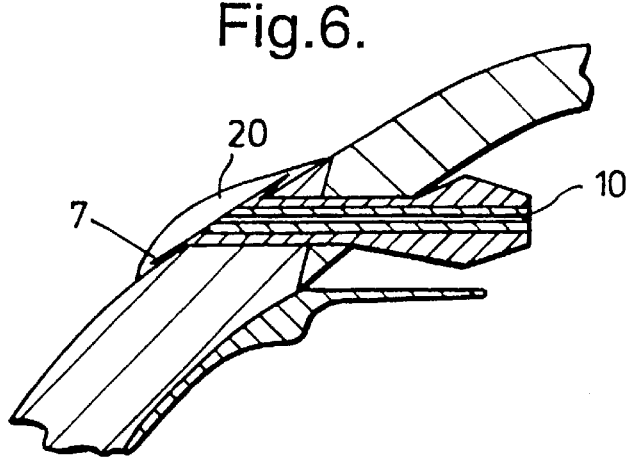
FIG. 6 is a schematic section through the eye at the sclerocorneal junction indicating the device of FIG. 1 in situ.

In the embodiment shown in FIGS. 1 to 6 the device is formed with an inner layer of a relatively hard material (e.g. a silicone elastomer) and an outer layer of a water swellable polymer. The swollen polymer of the outer layer is relatively soft and thus forms a compliant outer surface. The device shown is inserted in substantially unswollen (xerogel) state, whereby it swells in situ after implantation. The interior end section is able to swell to a greater extent than the body section as its expansion is unconstrained by external pressure from any tissue. The greater diameter interior end section as shown in FIG. 6, helps to retain the implant in position and prevent its extrusion through the GFS channel. The hydrogel's swelling also helps to seal the GFS channel against leakage of fluid immediately after surgery. The swellable polymer may be formed of a crosslinked copolymer of 2-(methacryloyloxy)ethyl 2-(trimethylammonium) ethyl phosphate inner salt and alkyl(alk)acrylate and/or hydroxy alkyl(alk) acrylate which is biocompatible, or of a less biocompatible swellable polymer which may be coated with a biocompatible polymer or otherwise treated to render it more biocompatible.

After forming the implant in the desired shape, it may be coated on all or some of its exposed surfaces with a biocompatible coating consisting of a polymer including 2-(methacryloyloxyethyl)-2'-(trimethylammonium)ethyl phosphate inner salt: dodecyl methacrylate: 3-(trimethoxysilyl)propyl methacrylate synthesised using the techniques described in WO-A-93/01221, and coated from a solution in methanol or ethanol and heated, optionally with a catalyst, to cross-link the polymer thereby coating all the internal and external walls of the device. Subsequently the plug 13 is fitted into the passageway. Since the plug has an external diameter slightly greater than the internal diameter of the passageway 10 and is resilient, the friction against the internal wall retains the plug in place until laser ablation. If necessary the plug may be retained in position using an adhesive between the plug and the internal wall of the passageway 10.

The taper of the body section in addition to the swellability of the outer layer improves the retention of the device, minimising the chance of its being extruded out of the eye once implanted. The flange limits inward movement during and after surgery, to prevent inward displacement of the device.

The device illustrated in FIGS. 1 to 4 is intended for anterior filtration, that is for filtration immediately posterior to the limbus, that is the anatomic junction between the cornea and sclera. The device is for insertion ab externo FIG. 5 illustrates the insertion procedure for the device.

In FIG. 5a, the conjunctiva is recessed as for trabeculectomy with a fornix based flap 20. Subsequently, as shown in FIG. 5b, the filtration area, 21 is treated with an antimetabolite, or by radiotherapy, which limits the local wound healing response. In FIG. 5c, a standard sized slit incision 22 is formed under the flap 20, using a keratome, the incision extending into the anterior chamber, the exit into which is shown as broken line 23. The filtration implant of FIGS. 1 to 4 is subsequently inserted from the outside (ab externo) through the slit incision. The tapered interior end assists insertion of the implant through the slit incision. The device is inserted until the flange lies against the edge of the slit incision. The likelihood of extrusion is minimised by the tapered shape of the body section and swelling of the outer layer of the body section, as explained above. The length is adapted for extending to the anterior chamber through the inner extent of the slit incision, so that the passageway 10 is in fluid communication with the anterior chamber. At the end of surgery the flap 20 of conjunctiva is closed and secured at the limbus.

Figure 7:
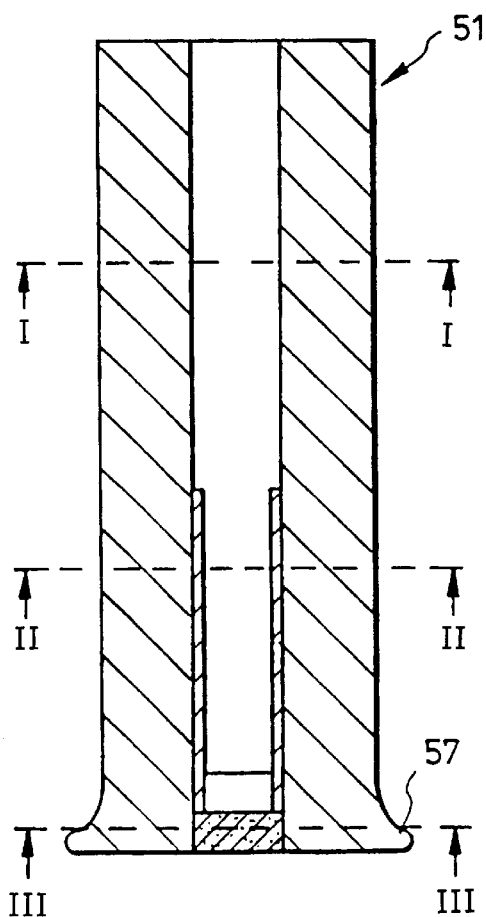
FIG. 7 is a transverse section through a further embodiment of glaucoma filtration implant according to the present invention, which is adapted for posterior filtration.

FIG. 7 shows a further embodiment of a device according to the present invention which is designed for posterior filtration. The implant 51 comprises a body section 52, an interior end section 54 and an exterior end section 53. The body section 5 is cylindrical, whilst exterior end section 5 has a generally conical taper 64.

Interior end section 3 comprises a flange 57 which is an oval washer-shaped annulus at an angle to the axis of the body section (in a similar manner to the flange at the interior end section of the device of FIGS. 1 to 4).

Figure 9A:
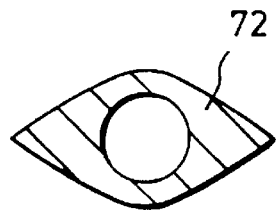
FIGS. 9a–c are cross sections along lines A—A, B—B and C—C, respectively of FIGS. 7 and 8.
Figure 9B:
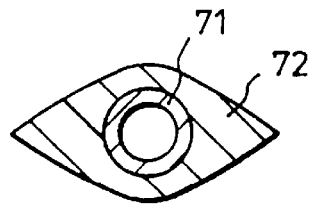
Figure 9C:
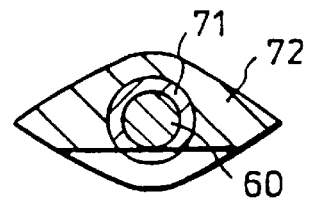

As is more clearly shown in FIGS. 9a–c, the exterior periphery of the device is oblong, that is the section is wider than it is high. The device is formed of various consistent parts. Towards the interior end section 54 there is an inner relatively stiff internal tubular section 71 and a relatively soft exterior wall section 72. The relatively hard reinforcing tube 71 extends along only a part of the length of the device 51, whilst the outer, relatively soft material 72 extends from the interior end section 54 to the exterior end section 53. The reinforcing tube 71 has circular cylindrical inner and outer walls throughout its length. The exterior relatively soft component 72 is formed directly on the outer surface of the reinforcing section 71 and forms the external periphery of the device itself.

In the interior end section 54 of the device there is a porous membrane 63 formed of a semi-permeable material acting as a flow inhibitor and a resistance element immediately upon insertion of the device, which completely covers the passageway 60 through the reinforcing tube 71. The membrane 63 is formed of a material which is sufficiently permeable to allow a low level of flow of intraocular fluid through the device immediately after surgery (i.e. is a resistance element) and is laser ablatable (i.e. is a removable flow inhibitor), so that it may be wholly or partially removed after the bleb has formed and flow is controlled by the bleb.

Figure 8:
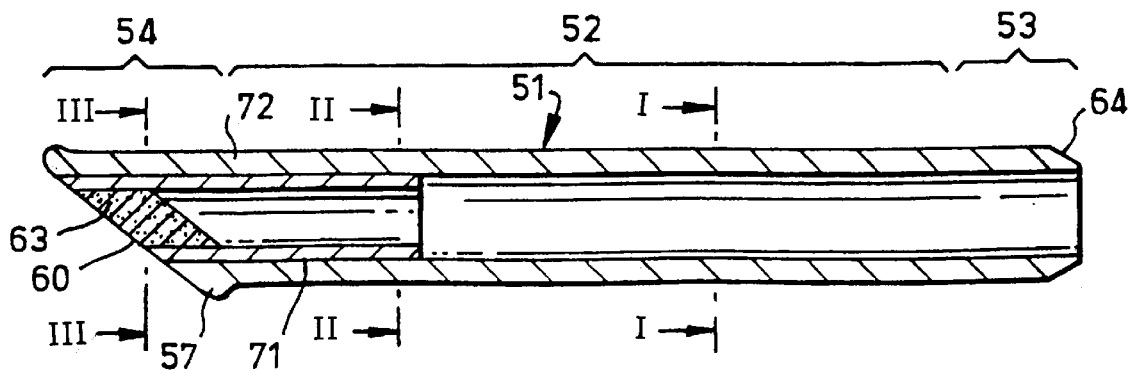
FIG. 8 is a longitudinal section through the device of FIG. 7.
Figure 12:
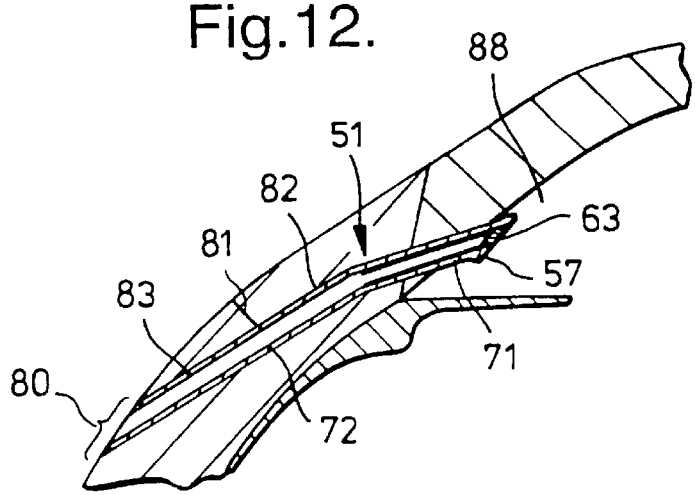
FIG. 12 is a section through the eye with the implant of FIGS. 7 to 9 in situ.

The material used to make the device of FIGS. 7 to 9 may comprise relatively hard and relatively soft silicone rubber materials to form the reinforcing component 71 and the softer, more flexible component 72. Whilst the flange is shown as being made of the same material as the relatively soft outer wall, 72 it may alternatively be formed of the relatively hard reinforcing material 71. The laser ablatable material may be formed of porous material, which may provide the desired permeability. Suitable materials which are laser ablatable are acrylic polymers. The material should preferably be formed of a bulk biocompatible material in order that, after laser ablation, any material of the plug which becomes exposed to tissue or fluid, should not generate an inflammation or wound healing response or encourage deposit of protein from the intraocular fluid to occlude the lumen.

Figure 10:
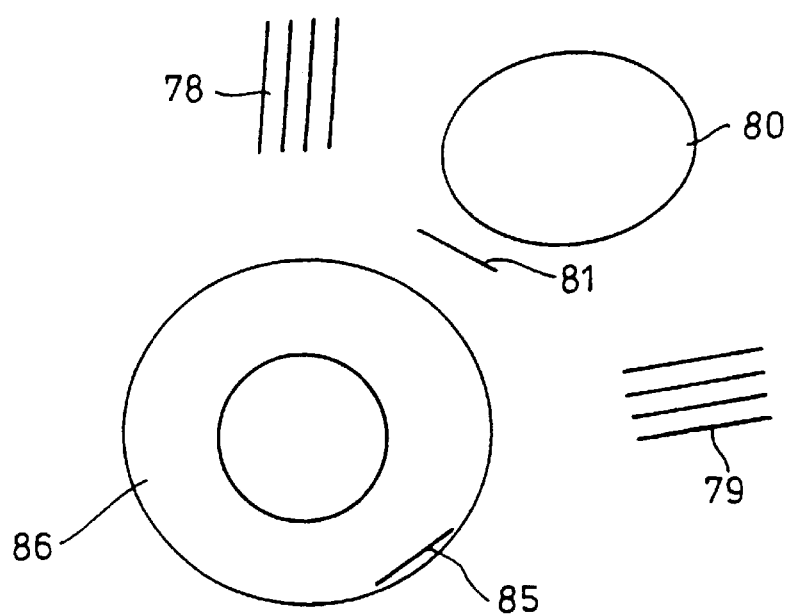
FIG. 10 is a schematic frontal view illustrating the procedure for inserting the device of FIGS. 7 to 9.

Because of the presence of the flange, and in order to minimise the size of the incision in which the implant is located, and because of ease of carrying out the surgery generating it is preferred for the device to be implanted ab interno. FIG. 10 is a schematic frontal view illustrating the procedure for implantation.

Figure 11:
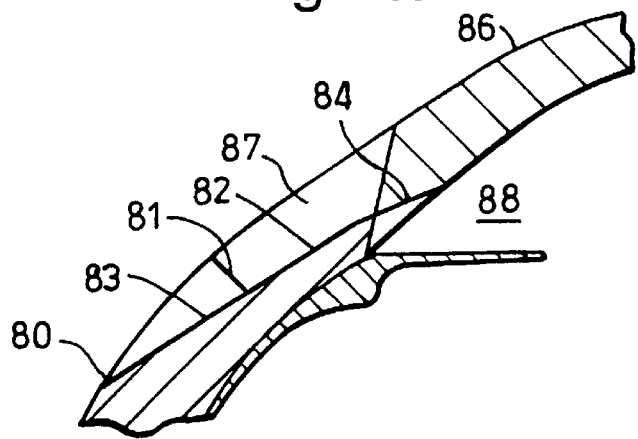
FIG. 11 is a schematic section through the eye illustrating the wound construction at the conjunctional incision illustrated in FIG. 10.

FIGS. 10 and 11 show the surgical incisions to be made during the insertion procedure. Initially the location of the conjunctival incision 81 is determined; it is placed at a distance posterior to the limbus, determined by the extent of any anterior conjunctival scarring. The location relative to the superior rectus 78 and horizontal rectus 79 muscles is indicated in FIG. 10. The intended filtration area 80, into which intraocular fluid drains through the implant, is exposed to antimetabilite drugs or B-irradiation. Subsequently a corneal paracentesis 85 is formed in the cornea 86, the paracentesis being at least one quadrant away from the intended conjunctival incision 81. The anterior chamber is filled with viscoelastic through the corneal paracentesis 85. This supports the eye during the subsequent insertion of the implant.

once the viscoelastic has been filled into the anterior chamber, the partial thickness scleral incision 81 is made using a shouldered knife. Then a crescent knife is used for anterior dissection 82 into clear cornea 87 and for posterior dissection 83 into the intended filtration area 80. Subsequently a keratome sized to accommodate the central section of the implant (longer diameter) is used to make incision 84 and enter anterior chamber 28 through cornea 86.

Figure 13:
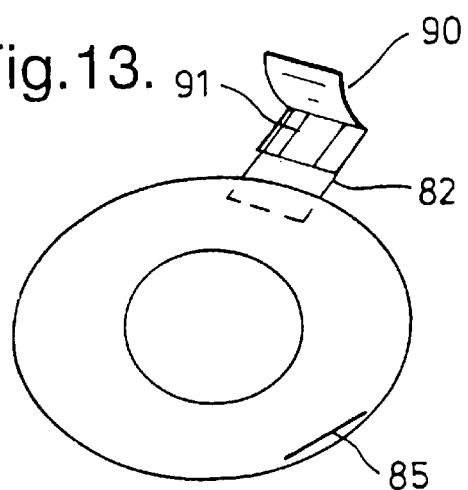
FIG. 13 is a schematic frontal view illustrating the procedure for inserting a glaucoma filtration implant adapted for choroidal filtration.
Figure 14:
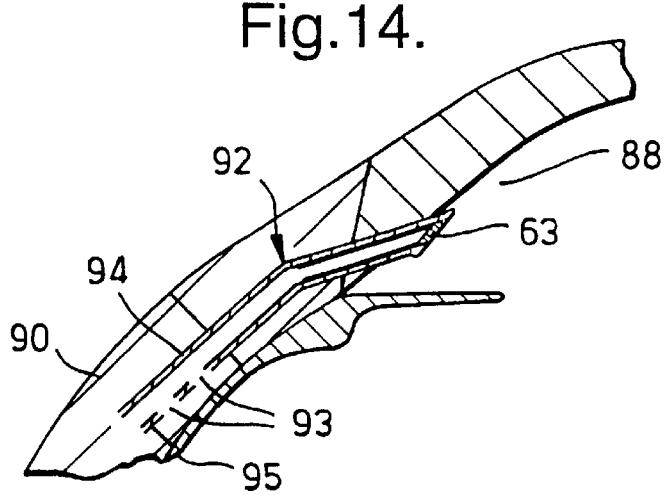
FIG. 14 is a schematic section through the eye at the sclerocorneal junction with the choroid filtration implant in position.

FIG. 13 is a schematic section through the implant 51 in position. It is implanted by passing a suture through the scleral tunnel 83, 82, 84 and out through the corneal paracentesis incision 85. The implant is then rail-roaded via the corneal paracentesis incision 85 and the anterior chamber 88 and into the scleral tunnel 84, 82, 81. The flange 57 at the interior end is flush with the inner wall of the anterior chamber 88. Extrusion of the device out from the eye is minimised by the flange 57. When the tube is in position the exterior end section is tucked through the posterior limb 83 of the scleral tunnel and, if necessary, trimmed flush with the scleral surface in the filtration area 80. The flexibility of the body section beyond the external end of the reinforcing tube 71 allows it to bend to fit the scleral tunnel 82, 83.

Immediately after insertion the plug 63 allows a low rate of flow of intraocular fluid from the anterior chamber 28 to the filtration area 80. After bleb formation has commenced in filtration area 80, the intraocular pressure will rise as a consequence of the reduce flow of intraocular fluid through the plug 63 (and, where it occurs, around the outside of the device through tunnel 83). When the IOP rises above the desired maximum, the plug 63 can be fully removed by the use of an ophthalmic laser, thereby reducing the resistance to flow of intraocular fluid and reducing the IOP stepwise so that it is again within the safe limits.

FIG. 13 shows the insertion procedure for a glaucoma filtration implant to be used for choroidal drainage. The technique is generally similar to that illustrated in FIGS. 10 and 11, except that instead of anterior incision 83 (shown in FIG. 11), a partial thickness scleral flap 90 is cut in a posterior direction. Under the flap a full thickness channel 91 is cut to expose the choroid. Then the standard slit incision 82 is cut into the anterior chamber using a keratome.

The implant device 92, which is similar to the device 51 for posterior filtration, is inserted in the same manner by railroading through the corneal incision 85 and the scleral tunnel 82. The exterior section of the implant is then trimmed to lie within the scleral bed 91 beneath the flap 90. The device 92 includes fenestrations 93 formed in the underside of the exterior end section of the flexible relatively soft component 94. These fenestrations 93 allow drainage of fluid over a greater surface area into the suprachoroidal space 95.

Figure 15:
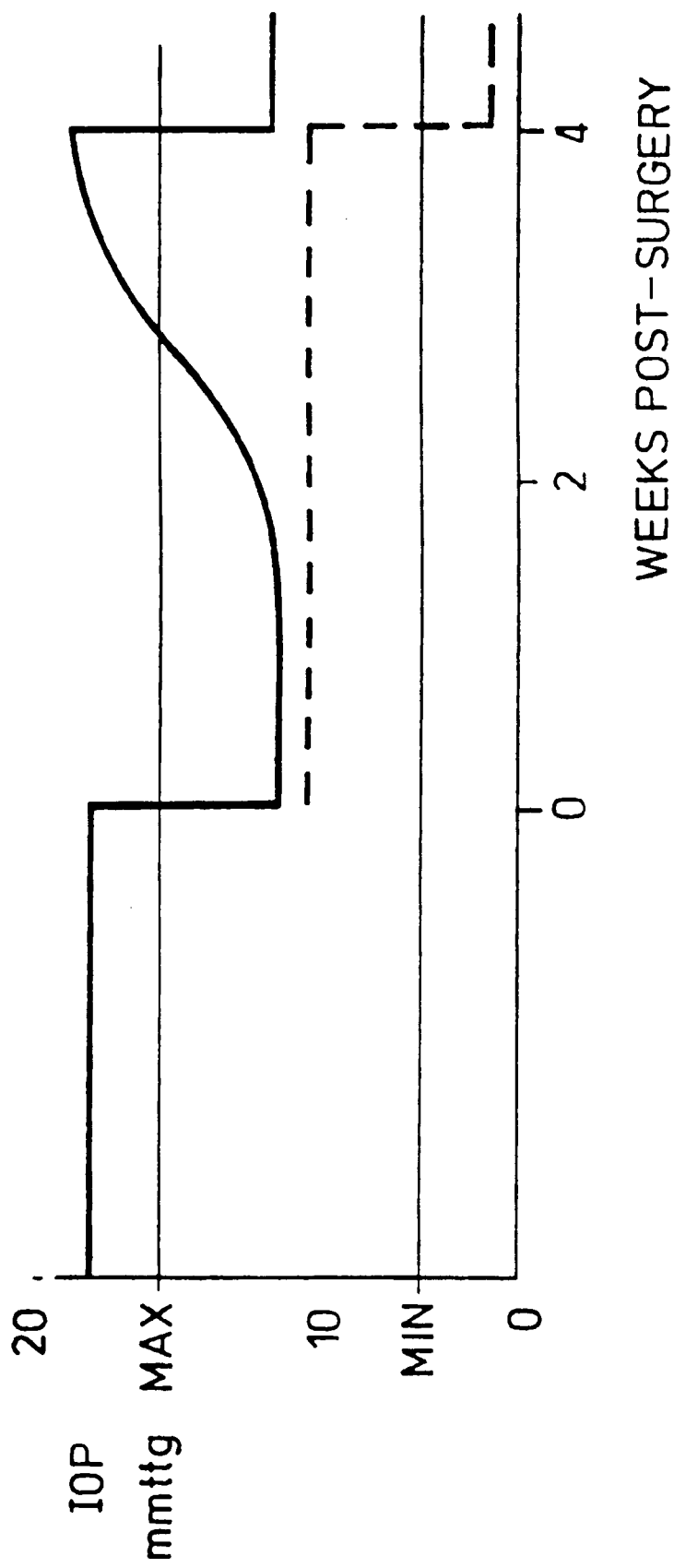
FIG. 15 shows the change in IOP after the implantation of a device according to the invention and removal of the flow inhibitor of such a device.
Figure 16:
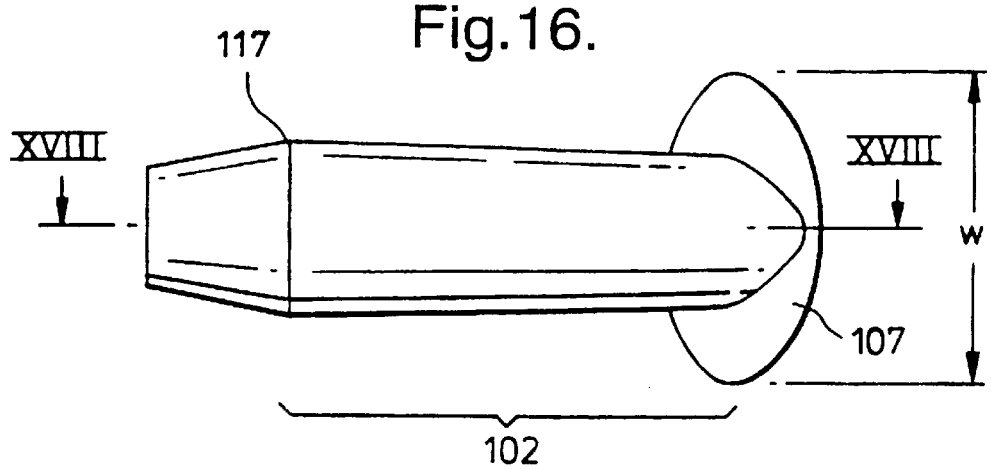
FIG. 16 is a top plan view of a further embodiment of a device according to the invention.
Figure 17:
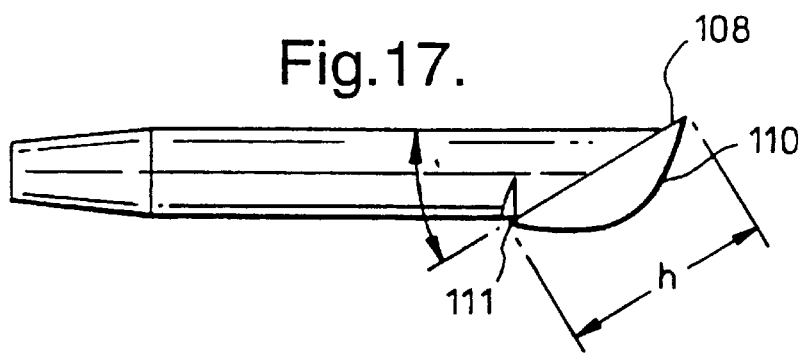
FIG. 17 is a side view of the device shown in FIG. 16.
Figure 18:
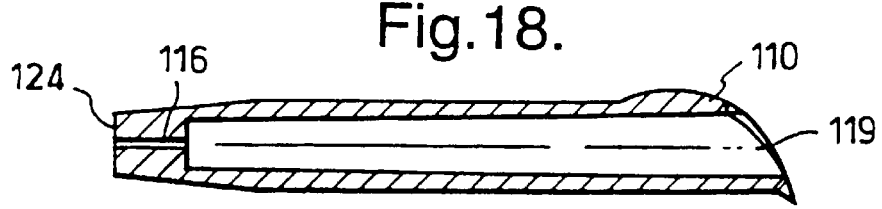
FIG. 18 is a section along line XVIII—XVIII of FIG. 16.
Figure 19:
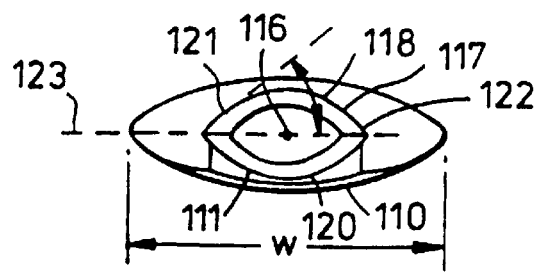
FIG. 19 is an end on view from the left hand end of the device of FIG. 16.

FIG. 15 illustrates the likely IOP values before and after insertion of any of the implants illustrated. Approximate safe values of IOP lie between the minimum and maximum lines shown in the graph. A patient for surgery has IOP above the safe maximum. At surgery, the IOP is reduced to a value within the safe range, when intraocular fluid flows through the unguarded bore 16 or the semi-permeable membrane 63 (and possibly around the outer wall of the implant through the scleral tunnel). As bleb formation takes place after about the second week after surgery, the IOP rises until it again reaches a value above the maximum. When the IOP reaches a value above the safe maximum, the plug 13 or membrane 63 can be ablated using an ophthalmic laser (usually YAG laser). The laser is directed through the cornea and the wall of the device surrounding the plug or membrane, which are transparent to the light, and focused at the plug or membrane. Ablation of the plug or membrane allows flow through the conduit formed by the opened passageway 10/60, the lumen 9 and the channel 12 out through the mouth 14 at the exterior end and into the filtration area 20/80. Thus the IOP is returned to a safe value.

FIGS. 16 to 19 illustrate a further embodiment of the device, which is generally a development of the device shown in FIGS. 1 to 4. In FIGS. 1 to 4, the taper of the body section 2 was in respect of the smaller diameter of the cross section. In the embodiment in FIGS. 16 to 19, the taper is of the largest diameter of the body section 102.

In this embodiment, the flange 107 is oblong in shape. Thus when viewed in a direction perpendicular to the back face, the width w is greater than the height h. Furthermore the face of the flange 110 facing away from the body section of the device is domed. At the lower end of the flange 111, the arrangement is such that the external surface of the device has no undercut section which has been found to be difficult to form, either by machining or moulding.

The device of the embodiment shown in FIGS. 16 to 19 is formed either by machining a blank formed by moulding a polymeric material into a shape having dimensions generally larger than the largest profile of the device and moulding the outer profile, or by moulding a blank to have the external peripheral shape of the device, followed in either case by drilling the lumen 119, for instance using a mechanical drill. Alternatively it may be possible to mould a blank with the desired external periphery and lumen.

The device is preferably made of a transparent material, for instance polymethylmethacrylate.

In this embodiment, the shape of the cross section of the body section, for instance at the internal end, comprises a pair of arcs 118 and 120 leading at each end to straight portions 121, 122. Straight portion 121 forms an angle with the line along the greatest diameter 123 of around 40°.

The embodiment of the invention shown in FIGS. 16 to 19 has no removable flow inhibitor. It has a resistant element 116, which is a small bore through the interior radial wall 124. The wall is, for instance, in the range 0.5 to 1 mm in thickness. The bore preferably has an internal diameter in the range 20 to 45 μm and is preferably formed using a laser drilling device.

The device shown in FIGS. 16 to 19 is around 5 mm in total length, with the widest diameter of the flange being around 2 to 2.5 mm, and the largest diameter perpendicular to the axis and the largest flange diameter is in the range 0.5 to 1.5 mm. The diameter of the lumen is preferably in the range 0.2 to 0.5 mm.

After the device has been formed including the laser drilled bore 116, it is coated with a biocompatible material, preferably from a liquid coating composition from which the solvent is removed after coating. Suitable coating polymers are described above.

What is claimed is:

1. A device for positioning in a slit aperture in the eye of a human or animal patient for relieving glaucoma, said device comprising:

an elongate body section having interior and exterior end sections at respective interior and exterior ends thereof;

at least one lumen extending through the body between the interior and exterior ends thereof;

wherein the exterior end section has a channel, one end of which has a mouth which opens to the outside of the eye and the other end of which is in fluid communication with at least one of said at least one lumen, and wherein the interior end section has a passageway, one end of which has a mouth opening into an internal chamber of the eye and the other end of which is in fluid communication with at least one of said at least one lumen, whereby the device has a conduit for fluid flowing from an internal chamber of the eye, which conduit extends through the passageway, the lumen and the channel and out to the outside of the eye, the body section being adapted for positioning in the slit aperture in the wall of the eye, the interior end section being adapted for being located so that it extends into an internal chamber of the eye and the exterior section being adapted for being located so that the mouth opens to the outside of the eye, wherein the conduit includes a removable flow inhibitor which inhibits flow in the conduit, wherein the body section has a cross section perpendicular to its axis which is the shape of an axial section through a bi-convex lens.

2. The device according to claim 1 in which said conduit includes a flow resistance element having a length $\lambda$ in $\mu$m, and a substantially circular cross section having diameter $\delta$ $\mu$m meeting the following requirements:

$$100 \leq \lambda \leq 5000$$
$$15 \leq \delta \leq 1000 \ \mu m$$
$$2 \times 10^{-4} \leq 1/\delta^4 \leq 2.5 \times 10^{-3}.$$

3. A device according to claim 1 in which the flow inhibitor is ablatable by an ophthalmic laser.

4. A device according to claim 3 wherein the material of the flow inhibitor is semi-permeable such that the rate of flow of intraocular fluid through the flow inhibitor at a pressure difference of 15 mmHg is in the range 1.4 to 3 m$\mu$l/minute.

5. The device according to claim 1 in which the ratio of the greatest diameter to that of the smallest diameter of the external periphery of the body section is in range (3 to 1.2):1.

6. A device according to claim 5, wherein said ratio is in the range (2.5 to 1.5):1.

7. The device according to claim 1 in which the shape and dimensions of the external periphery are constant along the length of the body section.

8. A device according to claim 1 in which the body section, along at least a part of its length, is formed of an external layer at the external surface and at least one internal layer, in which the external layer is resilient and has relatively low hardness, whilst the internal layer is formed of a material having a higher hardness.

9. The device of claim 1 in which all the tissue contacting surfaces of the device are formed of a biocompatible material, preferably a polymeric material in which the polymer includes pendant zwitterionic groups.

10. A device according to claim 9, wherein said polymer includes quaternary ammonium/phosphate ester zwitterionic groups.

11. A device according to claim 1 which further including a flange at the interior and/or exterior end thereof.

12. A device according to claim 11 in which the body section is tapered inwards towards end having the said flange.

13. A method for regulating the flow of fluid from an internal chamber of the eye of a human or animal patient, said method comprising:

forming a fluid escape channel from the internal chamber as a slit, inserting a device into the fluid escape channel such that a greatest diameter of the device is aligned with the slit, said device being for positioning in the slit for relieving glaucoma, said device comprising:

an elongate body section having interior and exterior end sections at respective interior and exterior ends thereof; and at least one lumen extending through the body section between the interior and exterior ends thereof, wherein the exterior end section has a further channel, one end of which has a mouth which opens to an outside of the device and the other end of which is in fluid communication with at least one of said at least one lumen, and wherein the interior end section has a passageway one end of which has a mouth opening into an internal chamber of the device and the other end of which is in fluid communication with at least one of said at least one lumen, whereby the device has a conduit for fluid flowing from an internal chamber of the eye, which conduit extends through the passageway, the lumen and the further channel, the body section being adapted for positioning in another channel in the wall of the eye, the interior end section being adapted for being located so that it extends into an internal chamber of the eye and the exterior end section being adapted for being located in use in a cavity, wherein the body section has a cross section perpendicular to its axis the perimeter of which is oblong having a longer diameter and a shortest diameter and forms a continuous convex curve;

said method further comprising:

allowing fluid to flow from the internal chamber of the eye through a conduit of said device and out through an exterior end of the device into another cavity.

14. A method according to claim 13 in which the internal chamber of the eye is the anterior chamber and in which the device relieves raised intraocular pressure.

15. A method according to 13 in which the device includes an ablatable flow inhibitor means within a passageway and in which the method includes the step of ablating the flow inhibitor after implantation of the device.

16. The device according to claim 1 in which said conduit includes a flow resistance element having a length $\lambda$ in $\mu$m, and a substantially circular cross section having diameter $\delta$ $\mu$m meeting the following requirements:

$$100 \leq \lambda \leq 5000$$
$$15 \leq \delta \leq 1000 \ \mu m$$
$$2 \times 10^{-4} \leq 1/\delta^4 \leq 2.5 \times 10^{-3}.$$

17. The device according to claim 1 wherein the flow inhibitor is ablatable by an ophthalmic laser.

18. A device for positioning in a slit aperture in the eye of a human or animal patient for relieving glaucoma, said device comprising:

an elongate body section having interior and exterior end sections at respective interior and exterior ends thereof;

at least one lumen extending through the body between the interior and exterior ends thereof;

wherein the exterior end section has a channel, one end of which has a mouth which opens to the outside of the eye and the other end of which is in fluid communication with at least one of said at least one lumen, and wherein the interior end section has a passageway, one end of which has a mouth opening into an internal chamber of the eye and the other end of which is in fluid communication with at least one of said at least one lumen, whereby the device has a conduit for fluid flowing from an internal chamber of the eye, which conduit extends through the passageway, the lumen and the channel and out to the outside of the eye, the body section being adapted for positioning in the slit aperture in the wall of the eye, the interior end section being adapted for being located so that it extends into an internal chamber of the eye and the exterior section being adapted for being located so that the mouth opens to the outside of the eye, wherein the conduit includes a removable flow inhibitor which inhibits flow in the conduit, wherein the body section has a cross section perpendicular to its axis the perimeter of which is oblong, having a longest diameter along a longitudinal axis thereof and a shortest diameter along a lateral axis thereof, the ratio of the longest diameter to the shortest diameter being in the range (1.5 to 2.5):1, the cross section being symmetrical about both longitudinal and lateral axes, and having a perimeter formed, on each side of said longitudinal axis of an arc of a circle, the end points of the arcs being joined at rounded intersection points, having a radius of curvature less than 0.25 times the radius of curvature of said arcs.

19. The device according to claim 18 in which said conduit includes a flow resistance element having a length $\lambda$ in $\mu$m, and a substantially circular cross section having diameter $\delta$ $\mu$m meeting the following requirements:

$$100 \leq \lambda \leq 5000$$

$$15 \leq \delta \leq 1000 \, \mu m$$

$$2 \times 10^{-4} \leq 1/\delta^4 \leq 2.5 \times 10^{-3}.$$

20. The device according to claim 18 wherein the flow inhibitor is ablatable by an ophthalmic laser.

21. A device for positioning in a slit aperture in the eye of a human or animal patient for relieving glaucoma, said device comprising:

an elongate body section having interior and exterior end sections at respective interior and exterior ends thereof;

at least one lumen extending through the body between the interior and exterior ends thereof;

wherein the exterior end section has a channel, one end of which has a mouth which opens to the outside of the eye and the other end of which is in fluid communication with at least one of said at least one lumen, and wherein the interior end section has a passageway, one end of which has a mouth opening into an internal chamber of the eye and the other end of which is in fluid communication with at least one of said at least one lumen, whereby the device has a conduit for fluid flowing from an internal chamber of the eye, which conduit extends through the passageway, the lumen and the channel and out to the outside of the eye, the body section being adapted for positioning in the slit aperture in the wall of the eye, the interior end section being adapted for being located so that it extends into an internal chamber of the eye and the exterior section being adapted for being located so that the mouth opens to the outside of the eye, wherein the conduit includes a removable flow inhibitor which inhibits flow in the conduit, wherein the body section has a cross section perpendicular to its axis the perimeter of which is oblong, having a longest diameter along a longitudinal axis thereof inserting a device into the fluid escape channel such that the longitudinal axis of the body section cross section is aligned with the slit, said device being for positioning in the slit for relieving glaucoma, said device comprising:

an elongate body section having interior and exterior end sections at respective interior and exterior ends thereof;

at least one lumen extending through the body between the interior and exterior ends thereof;

wherein the exterior end section has a channel, one end of which has a mouth which opens to the outside of the eye and the other end of which is in fluid communication with at least one of said at least one lumen, and wherein the interior end section has a passageway, one end of which has a mouth opening into an internal chamber of the eye and the other end of which is in fluid communication with at least one of said at least one lumen, whereby the device has a conduit for fluid flowing from an internal chamber of the eye, which conduit extends through the passageway, the lumen and the further channel and out to the outside of the eye, the body section being adapted for positioning in the slit aperture in the wall of the eye, the interior end section being adapted for being located so that it extends into an internal chamber of the eye and the exterior section being adapted for being located so that the mouth opens to the outside of the eye, wherein the conduit includes a removable flow inhibitor which inhibits flow in the conduit, and a shortest diameter along a lateral axis thereof, the ratio of the longest diameter to the shortest diameter being in the range (1.5 to 2.5):1, the perimeter of the cross section being formed of convex curves on each side of said longitudinal axis, and extending from said lateral axis towards the end, and further comprising straight sections extending from the convex curve towards each end forming an angle to said longitudinal axis of less than 30°.

22. The device according to claim 21 in which said conduit includes a flow resistance element having a length $\lambda$ in $\mu$m, and a substantially circular cross section having diameter $\delta$ $\mu$m meeting the following requirements:

$$100 \leq \lambda \leq 5000$$

$$15 \leq \delta \leq 1000 \, \mu m$$

$$2 \times 10^{-4} \leq 1/\delta^4 \leq 2.5 \times 10^{-3}.$$

23. The device according to claim 21 wherein the flow inhibitor is ablatable by an ophthalmic laser.

24. A device according to claim 23 wherein the body section has one or more straight sections each forming an angle in the range of 15° to 30° to the longitudinal axis.

25. A device according to claim 21 in which the straight sections extend to and join together at the longitudinal axis.

26. A device according to claim 21 in which the convex curves each form the arc of a circle having a radius, and in which said straight sections are connected via rounded intersections having radii of curvature less than 0.25 times the radius of said arc.

27. A method for regulating the flow of fluid from an internal chamber of the eye of a human or animal patient, said method comprising:

forming a fluid escape channel from the internal chamber as a slit,
wherein the body section has a cross section perpendicular to its axis which is the shape of an axial section through a bi-convex lens;

said method further comprising:

allowing fluid to flow from the internal chamber of the eye through a conduit of said device and out through a conduit of said device and out through an exterior end of the device to the outside of the eye.

28. A method according to claim 27 wherein the internal chamber of the eye is the anterior chamber and wherein the device relieves raised intraocular pressure.

29. A method according to claim 27 wherein said flow inhibitor means is ablatable and wherein said method includes ablating the ablatable flow inhibitor after implantation of the device.

30. A method for regulating the flow of fluid from an internal chamber of the eye of a human or animal patient, said method comprising:

forming a fluid escape channel from the internal chamber as a slit, inserting a device into the channel such that the longitudinal axis of the body section cross section is aligned with the slit, said device being for positioning in the slit for relieving glaucoma, said device comprising:

an elongate body section having interior and exterior end sections at respective interior and exterior ends thereof;

at least one lumen extending through the body between the interior and exterior ends thereof;

wherein the exterior end section has a further channel, one end of which has a mouth which opens to the outside of the eye and the other end of which is in fluid communication with at least one of said at least one lumen, and wherein the interior end section has a passageway, one end of which has a mouth opening into an internal chamber of the eye and the other end of which is in fluid communication with at least one of said at least one lumen, whereby the device has a conduit for fluid flowing from an internal chamber of the eye, which conduit extends through the passageway, the lumen and the further channel and out to the outside of the eye, the body section being adapted for positioning in the slit aperture in the wall of the eye, the interior end section being adapted for being located so that it extends into an internal chamber of the eye and the exterior section being adapted for being located so that the mouth opens to the outside of the eye, wherein the conduit includes a removable flow inhibitor which inhibits flow in the conduit, wherein the body section has a cross section perpendicular to its axis the perimeter of which is oblong, having a longest diameter along a longitudinal axis thereof and a shortest diameter along a lateral axis thereof, the ratio of the longest diameter to the shortest diameter being in the range (1.5 to 2.5):1, the cross section being symmetrical about both longitudinal and lateral axes, and having a perimeter formed, on each side of said longitudinal axis of an arc of a circle, the end points of the arcs being joined at rounded intersection points, having a radius of curvature less than 0.25 times the radius of curvature of said arcs;

said method further comprising:

allowing fluid to flow from the internal chamber of the eye through a conduit of said device and out through a conduit of said device and out through an exterior end of the device to the outside of the eye.

31. A method according to claim 30 wherein the internal chamber of the eye is the anterior chamber and wherein the device relieves raised intraocular pressure.

32. A method according to claim 30 wherein said flow inhibitor means is ablatable and wherein said method includes ablating the ablatable flow inhibitor after implantation of the device.

33. A method for regulating the flow of fluid from an internal chamber of the eye of a human or animal patient, said method comprising:

forming a fluid escape channel from the internal chamber as a slit, inserting a device into the channel such that the longitudinal axis of the body section cross section is aligned with the slit, said device being for positioning in the slit for relieving glaucoma, said device comprising:

an elongate body section having interior and exterior end sections at respective interior and exterior ends thereof;

at least one lumen extending through the body between the interior and exterior ends thereof;

wherein the exterior end section has a further channel, one end of which has a mouth which opens to the outside of the eye and the other end of which is in fluid communication with at least one of said at least one lumen, and wherein the interior end section has a passageway, one end of which has a mouth opening into an internal chamber of the eye and the other end of which is in fluid communication with at least one of said at least one lumen, whereby the device has a conduit for fluid flowing from an internal chamber of the eye, which conduit extends through the passageway, the lumen and the further channel and out to the outside of the eye, the body section being adapted for positioning in the slit aperture in the wall of the eye, the interior end section being adapted for being located so that it extends into an internal chamber of the eye and the exterior section being adapted for being located so that the mouth opens to the outside of the eye, wherein the conduit includes a removable flow inhibitor which inhibits flow in the conduit, wherein the body section has a cross section perpendicular to its axis the perimeter of which is oblong, having a longest diameter along a longitudinal axis thereof and a shortest diameter along a lateral axis thereof, the ratio of the longest diameter to the shortest diameter being in the range (1.5 to 2.5):1, the perimeter of the cross section being formed of convex curves on each side of said longitudinal axis, and extending from said lateral axis towards the end, and further comprising straight sections extending from the convex curve towards each end forming an angle to said longitudinal axis of less than 30°;

said method further comprising:
   allowing fluid to flow from the internal chamber of the eye through a conduit of said device and out through a conduit of said device and out through an exterior end of the device to the outside of the eye.

34. A method according to claim 33 wherein the internal chamber of the eye is the anterior chamber and wherein the device relieves raised intraocular pressure.

35. A method according to claim 33 wherein said flow inhibitor means is ablatable and wherein said method includes ablating the ablatable flow inhibitor after implantation of the device.

* * * * *